(12) United States Patent
Ceccarini et al.

(10) Patent No.: US 7,267,991 B2
(45) Date of Patent: Sep. 11, 2007

(54) METHOD FOR ESTIMATING THE SULFUR CONTENT IN THE FUEL OF AN INTERNAL COMBUSTION ENGINE

(75) Inventors: Daniele Ceccarini, Rimini (IT); Matteo De Cesare, Torremaggiore (IT); Luca Poggio, Spinetta Marengo (IT)

(73) Assignee: Magneti Marelli Powertrain S.p.A., Turin (IT)

(*) Notice: Subject to any disclaimer, the term of this patent is extended or adjusted under 35 U.S.C. 154(b) by 648 days.

(21) Appl. No.: 10/316,736

(22) Filed: Dec. 11, 2002

(65) Prior Publication Data

US 2003/0134425 A1    Jul. 17, 2003

(30) Foreign Application Priority Data

Dec. 14, 2001    (IT)  ............................... BO01A0762

(51) Int. Cl.
*G01V 31/00*    (2006.01)
(52) U.S. Cl. ............................. 436/119; 60/284; 60/286
(58) Field of Classification Search .................. 60/284, 60/286, 285; 436/119
See application file for complete search history.

(56) References Cited

U.S. PATENT DOCUMENTS 6,293,094 B1    9/2001    Schmidt et al.

FOREIGN PATENT DOCUMENTS

| DE | 198 44 178 A1 | 3/2000 |
|---|---|---|
| EP | 0 580 389 A1 | 1/1994 |
| EP | 1 148 215 A1 | 10/2001 |
| WO | WO 01/49988 A1 | 7/2001 |

*Primary Examiner*—Jill Warden
*Assistant Examiner*—Samuel P. Siefke
(74) *Attorney, Agent, or Firm*—Chapman and Cutler LLP

(57) ABSTRACT

A method for estimating the sulfur content in the fuel of an internal combustion engine equipped with a catalyser; the percentage of sulfur present in the fuel supplied during a specific measurement time interval is estimated by dividing the quantity of sulfur stored in the catalyser during the measurement time interval by the product of a fixed conversion constant and the mass of fuel supplied to the cylinder in the measurement time interval.

12 Claims, 1 Drawing Sheet

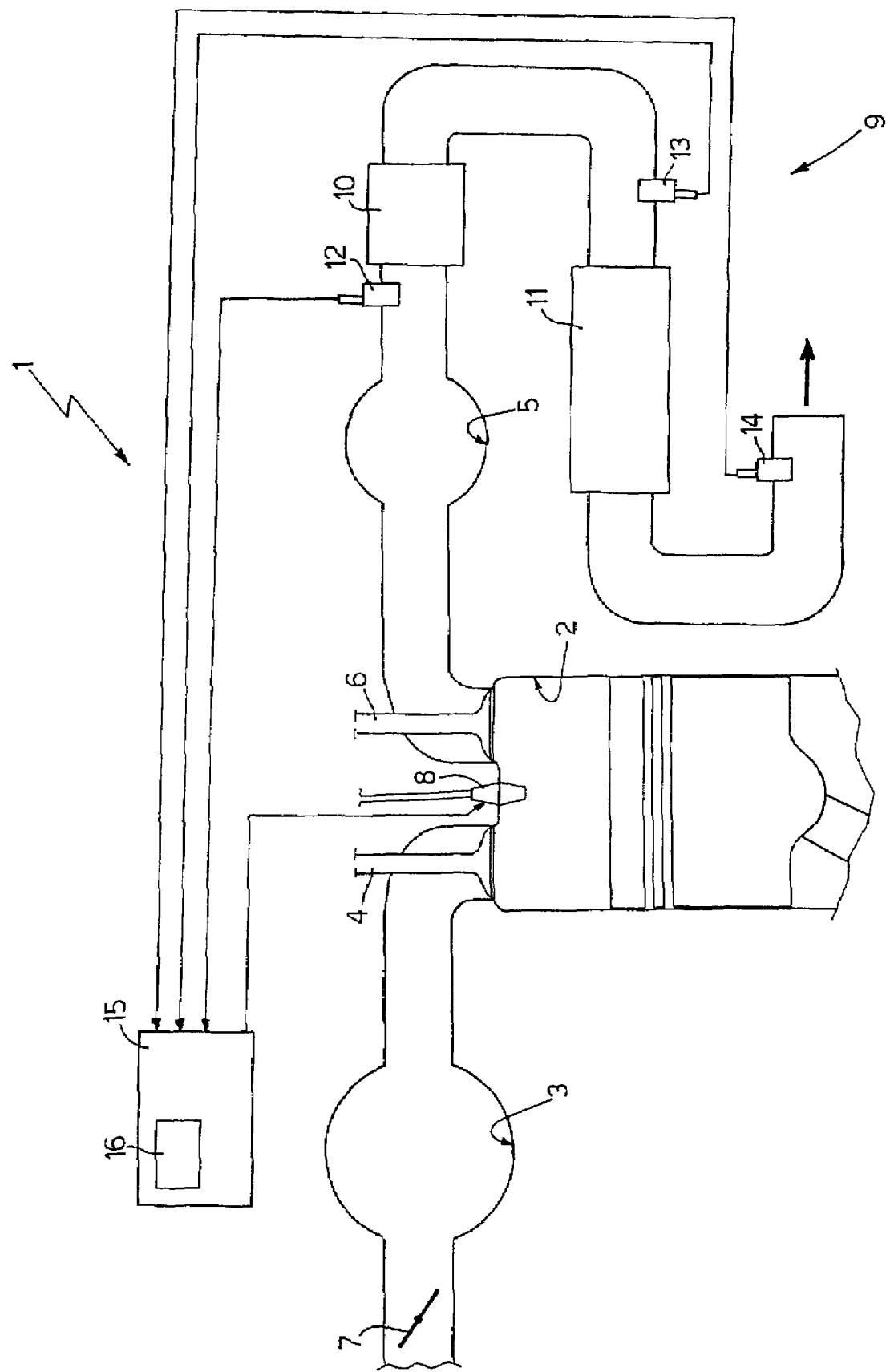

METHOD FOR ESTIMATING THE SULFUR CONTENT IN THE FUEL OF AN INTERNAL COMBUSTION ENGINE

The present invention relates to a method for estimating the sulfur content in the fuel of an internal combustion engine.

The present invention is advantageously applied in the automotive internal combustion engine sector, to which the following description makes explicit reference without thereby restricting the general scope thereof.

BACKGROUND OF THE INVENTION

Modern automotive internal combustion engines comprise an exhaust pipe that terminates in a catalyser, which has the function of reducing levels of pollutants contained in the exhaust gas; in particular, the catalyser stores either the $NO_x$ groups produced during combustion, or the sulfur (in the form of $SO_x$), which is contained in the fuel and is released during combustion. The catalyser has limited storage capacity for $NO_x$ groups and sulfur (such storage capacity generally amounts to 3-5 grams) and when said storage capacity is exhausted, the catalyser must be cleaned by means of a regeneration process.

The total mass of $NO_x$ groups produced during combustion is much greater than the mass of sulfur released during combustion, and moreover the regeneration process to remove $NO_x$ groups (a few seconds of rich combustion) is much shorter than the regeneration process to remove sulfur (at least two minutes of rich combustion combined with an internal temperature in the catalyser which, in relative terms, is very high). For the reasons stated above, the regeneration process to remove $NO_x$ groups is normally carried out every 45-75 seconds of engine operation, while the regeneration process to remove sulfur is normally carried out every 6-10 hours of engine operation.

In particular, the actual residual capacity available in the catalyser for storing $NO_x$ groups is estimated periodically according to the time elapsed since the preceding regeneration process to remove sulfur and according to the sulfur content of the fuel, and performance of the regeneration process to remove sulfur is scheduled on the basis of said estimate of residual capacity.

Fuel manufacturers guarantee the maximum sulfur content of fuel (for example in Italy said value is currently 150 ppm); however, the actual sulfur content is very often below said maximum value, such that using the maximum value results in an, often very significant, overestimate of sulfur content, so resulting in a greater frequency of regeneration, which entails both increased consumption and greater irregularity in engine operation. Moreover, the maximum sulfur content in fuel varies from country to country, as a result of which an engine calibrated to use a fuel in one country might not operate optimally with fuel from another country.

In order to resolve the problems described above, it has been proposed to use a sensor capable of directly measuring the actual sulfur content of the fuel; however, said sensor is particularly expensive and normally requires frequent calibration to provide accurate measurements.

SUMMARY OF THE INVENTION

The aim of the present invention is to provide a method for estimating the sulfur content in the fuel of an internal combustion engine, which method does not have the above-stated disadvantages and, in particular, is simple and economic to implement.

The present invention provides a method for estimating the sulfur content in the fuel of an internal combustion engine equipped with at least one cylinder and at least one catalyser, the latter being capable of storing a quantity of sulfur and $NO_x$ groups and being subjected to a regeneration process to remove $NO_x$ groups when efficiency of the catalyser itself falls outside an acceptable range; the method providing a determination of the percentage of sulfur present in the fuel supplied during a specific measurement time interval by dividing the quantity of sulfur stored in the catalyser during the measurement time interval by the product of a fixed conversion constant and the mass of fuel supplied to the cylinder in the measurement time interval; the method being characterised in that a first quantity of $NO_x$ groups stored by the catalyser immediately before a regeneration process to remove $NO_x$ groups is estimated at the beginning of the measurement time interval, a second quantity of $NO_x$ groups stored by the catalyser immediately before a regeneration process to remove $NO_x$ groups is estimated at the end of the measurement time interval and said quantity of sulfur stored in the catalyser during the measurement time interval is estimated from the difference between said first quantity of $NO_x$ groups and said second quantity of $NO_x$ groups.

The present invention also provides a method for estimating the quantity of sulfur stored in a catalyser of an internal combustion engine equipped with at least one cylinder; the catalyser being capable of storing a quantity of sulfur and $NO_x$ groups and being subjected to a regeneration process to remove $NO_x$ groups when efficiency of the catalyser itself falls outside an acceptable range; the method being characterised in that a first quantity of $NO_x$ groups stored by the catalyser immediately before a regeneration process to remove $NO_x$ groups is estimated at the beginning of the measurement time interval, a second quantity of $NO_x$ groups stored by the catalyser immediately before a regeneration process to remove $NO_x$ groups is estimated at the end of the measurement time interval and the quantity of sulfur stored in the catalyser during the measurement time interval is estimated from the difference between said first quantity of $NO_x$ groups and said second quantity of $NO_x$ groups.

The present invention also provides a method for estimating the sulfur content in the fuel of an internal combustion engine equipped with at least one cylinder and at least one catalyser, the latter being capable of storing a quantity of sulfur and $NO_x$ groups and periodically being subjected to a regeneration process to remove sulfur; the method providing the use of a current sulfur concentration value and the correction of said sulfur concentration value in order to obtain a new sulfur concentration value; the method being characterised in that a first time interval, which is actually necessary to complete a regeneration process to remove sulfur, is measured, the quantity of sulfur stored in the catalyser before said regeneration process to remove sulfur is determined using said current sulfur concentration value, a second time interval, which is theoretically necessary to complete the regeneration process, is estimated on the basis of the estimated quantity of sulfur stored in the catalyser, and a multiplicative correction coefficient is determined as a ratio between said first time interval and said second time interval.

BRIEF DESCRIPTION OF THE DRAWING

The present invention will now be described with reference to the attached drawing, which illustrates a non-limiting embodiment thereof; in particular, the attached FIGURE is a schematic diagram of an internal combustion engine operating in accordance with the estimation method provided by the present invention.

DETAILED DESCRIPTION OF THE INVENTION

In the attached FIGURE, 1 denotes the overall internal combustion engine equipped with four cylinders 2 (only one of which is shown in FIG. 1), each of which is connected to an intake manifold 3 via at least one respective intake valve 4 and to an exhaust manifold 5 via at least one respective exhaust valve 6. The intake manifold 3 receives fresh air (i.e. air originating from the outside environment and containing approximately 20% oxygen) via a throttle valve 7, which can be adjusted between a closed position and a maximally open position. The fuel (for example petrol, diesel oil, methane or LPG) is directly injected into each cylinder 2 by a respective injector 8.

An exhaust pipe 9 leads from the exhaust manifold 5, said exhaust pipe comprising a precatalyser 10 and a subsequent catalyser 11; inside the exhaust pipe 9 there is installed a UEGO probe 12, which is arranged upstream from the catalytic preconverter 10 and is capable of detecting the quantity of oxygen present in the exhaust gases input into the catalytic preconverter 10, a temperature sensor 13, which is arranged between the catalytic preconverter 10 and catalyser 11 and is capable of detecting the temperature of the gas input into the catalyser 11, and a multisensor 14, which is arranged downstream from the catalyser 11 and is capable of detecting either the presence of $NO_x$ groups (nitrogenous group sensor) or the quantity of oxygen present relative to stoichiometric conditions (lambda probe) in the exhaust gases output from the catalyser 11 (i.e. in the exhaust gases released from the exhaust pipe 9 into the atmosphere).

The engine 1 furthermore comprises a control unit 15 which, inter alia, on each cycle controls the throttle valve 7 and the injector 8 in order to fill the cylinders 2 with a quantity of a blend of combustion agent (fresh air) and fuel in a specific ratio as a function of the operating conditions of the engine 1 and as a function of the commands received from the driver. In order to allow the control unit 15 to acquire the data required for correct operation thereof, the control unit 15 is connected to the UEGO probe 12, the temperature sensor 13 and the multisensor 14.

In service, the catalyser 11 stores either the $NO_x$ groups produced during combustion or the sulfur (in the form of $SO_x$) contained in the fuel and released during combustion in order to prevent said constituents from being released directly into the atmosphere. Periodically, the control unit 15 calculates an index I of deterioration in performance of the catalyser 11, which index I is capable of indicating the efficiency with which the catalyser 11 itself is operating.

The deterioration index I is stated as a percentage and is calculated from the ratio between the quantity $NO_{xloss}$ of $NO_x$ groups not captured by the catalyser 11 and released directly into the atmosphere and the quantity $NO_{xtotal}$ of $NO_x$ groups produced by the engine 1; obviously, the higher the deterioration index I, the poorer the performance of the catalyser 11. The quantity $NO_{xloss}$ of $NO_x$ groups not captured by the catalyser is obtained directly by the control unit 15 by measurement, performed by the multisensor 14, of the exhaust gases released from the exhaust pipe 9 into the atmosphere, while the quantity $NO_{xtotal}$ of $NO_x$ groups produced by the engine 1 is obtained in substantially known manner by the control unit 15 using maps that state the specific quantity (i.e. the quantity per unit of fuel injected into the cylinders 2) of $NO_x$ groups produced by the engine 1 as a function of engine status (typically as a function of engine speed and as a function of delivered torque).

The catalyser 11 has a limited storage capacity for $NO_x$ groups and sulfur (such storage capacity normally amounts to 4 grams) and when said storage capacity is exhausted, the catalyser 11 has to be cleaned by means of a regeneration process. The total mass of $NO_x$ groups produced during combustion is much greater than the mass of sulfur released during combustion, and moreover the regeneration process to remove $NO_x$ groups (a few seconds of rich combustion of the engine 1) is much shorter than the regeneration process to remove sulfur (at least two minutes of rich combustion of the engine 1 combined with an internal temperature in the catalyser 11 which, in relative terms, is very high). For the reasons stated above, the regeneration process to remove $NO_x$ groups is normally carried out every 45-75 seconds of operation of the engine 1, while the regeneration process to remove sulfur is normally carried out every 6-10 hours of operation of the engine 1.

In particular, the regeneration process to remove sulfur is scheduled by the control unit 15 according to the percentage value S of sulfur contained in the fuel and according to the time that has elapsed since the last regeneration process to remove sulfur, while the regeneration process to remove $NO_x$ groups is carried out by the control unit 15 every time the index I of deterioration in performance of the catalyser 11 is greater than a preset threshold value (for example 20%), since, under normal conditions, the deterioration index I tends to get worse (i.e. increase) as the storage capacity of the catalyser 11 approaches saturation.

From the above explanation, it is clear that the total mass Mstored stored in the catalyser 11 is given by the sum of the quantity $SO_{xstored}$ of stored sulfur, measured in $NO_x$ equivalents, and of the quantity $NO_{xstored}$ of stored $NO_x$ groups, and that the catalyser 11 is no longer capable of capturing further sulfur or $NO_x$ groups, i.e. is no longer capable of operating properly, once the total mass $M_{stored}$ stored has come to equal the total storage capacity of the catalyser 11 itself.

The control unit 15 is equipped with an estimator 16, which is capable of supplying the control unit 15 itself with an estimate of the percentage S of sulfur present in the fuel used by the engine 1, so as to allow the control unit 15 to schedule correctly the regeneration processes for the catalyser 11 in order to achieve either reduced overall consumption of the engine 1 or reduced emissions of pollutants into the atmosphere.

When the engine 1 is relatively new, i.e. when the catalyser 11 is new and has not deteriorated, the estimator 16 is capable of directly estimating the value of the percentage S of sulfur present in the fuel used by the engine 1; this function is of particular value for rapidly obtaining a starting value for the percentage S of sulfur.

The percentage S of sulfur present in the fuel supplied during a specific measurement time interval is estimated by the estimator 16 by applying equation [1], in which $SO_{xstored}$ is the quantity of sulfur stored in the catalyser 11 during the measurement time interval, $K_{SOx}$ is a fixed conversion constant and mfuel is the mass of fuel supplied to the cylinders 2 in the measurement time interval.

$$S = \frac{SOx_{stored}}{K_{SOx} \cdot m_{fuel}} \quad [1]$$

The equation [1] is valid on the assumption that the sulfur contained in the fuel is completely retained within the catalyser 11; this assumption substantially always applies, except for negligible errors during normal operation of the engine 1. Analysis of the equation [1] reveals that the value for the conversion constant $K_{SOx}$ can readily be determined theoretically and the value for the mass mfuel of fuel supplied to the cylinders 2 in the measurement time interval can be determined easily and accurately by the control unit 15 on the basis of the commands issued to the injectors 8; it is thus clear that, once the value for the quantity SOxstored of sulfur stored in the catalyser 11 has been estimated, the percentage S of sulfur can easily be calculated.

The quantity $SO_{xstored}$ of sulfur stored in the catalyser 11 in a certain measurement time interval can be estimated by comparing the regeneration process to remove $NO_x$ groups at the beginning of the measurement time interval and the regeneration process to remove $NO_x$ groups at the end of the measurement time interval and assuming that the difference detected in the quantity of stored $NO_x$ groups is entirely due to the quantity SOxstored of sulfur stored in the catalyser 11; as stated above, this assumption is valid if the catalyser 11 has not deteriorated and there is no drift in the model of the $NO_x$ groups, i.e. when the catalyser 11 is substantially new.

In other words, it is assumed that, during the measurement time interval, the storage capacity of the catalyser 11 does not vary, i.e. it is assumed that the regeneration process to remove $NO_x$ groups at the beginning of the measurement time interval and the regeneration process to remove $NO_x$ groups at the end of the measurement time interval proceed on the basis of the same value for total mass $M_{stored}$ stored in the catalyser 11. Since the total mass $M_{stored}$ stored in the catalyser 11 is given by the sum of the quantity $SO_{xstored}$ of stored sulfur, measured in $NO_x$ equivalents, and of the quantity $NO_{xstored}$ of stored $NO_x$ groups, it is obvious that the difference found between the quantities $NO_{xstored}$ of stored $NO_x$ groups amounts to the quantity $SO_{xstored}$ of stored sulfur.

The quantity $NO_{xstored}$ of stored $NO_x$ groups relating to the regeneration process to remove $NO_x$ at the beginning of the measurement time interval and relating to the regeneration process to remove $NO_x$ groups at the end of the measurement time interval can be estimated by subtracting from the quantity $NO_{xtotal}$ of $NO_x$ groups produced by the engine 1 the quantity $NO_{xloss}$ of $NO_x$ groups not captured by the catalyser 11 and released directly into the atmosphere. As stated above, the quantity $NO_{xloss}$ of $NO_x$ groups not captured by the catalyser is obtained directly by the control unit 15 by measurement, performed by the multisensor 14, of the exhaust gases released from the exhaust pipe 9 into the atmosphere, while the quantity $NO_{xtotal}$ of $NO_x$ groups produced by the engine 1 is obtained in a substantially known manner by the control unit 15 using maps that state the specific quantity (i.e. the quantity per unit of fuel injected into the cylinders 2) of $NO_x$ groups produced by the engine 1 as a function of engine status (typically as a function of engine speed and as function of delivered torque).

Under normal operating conditions, i.e. when the catalyser 11 is not new, the estimator 16 is capable of adapting a current sulfur concentration value $SO_{old}$ by applying—where necessary—a correction to said current value $S_{old}$ in order to obtain a new sulfur concentration value $S_{new}$.

The size of the above-stated correction to the current sulfur concentration value $S_{old}$ can be estimated during the regeneration process to remove sulfur, during which the engine 1 is caused to operate in rich combustion, by applying equation [2], in which $t_0$ is the starting time for the regeneration process, $t_1$ is the measured real time at which the multisensor 14 detects a change from lean ($\lambda$ less than 1) to rich ($\lambda$ greater than 1), and $t_2$ is the theoretical, estimated time at which the multisensor 14 ought to detect a change from lean ($\lambda$ less than 1) to rich ($\lambda$ greater than 1) if the current sulfur concentration value $S_{old}$ were correct. The value of time $t_2$ is easily calculated by calculating the total quantity of sulfur present in the fuel injected into the cylinders 2 since the preceding regeneration process to remove sulfur and assuming that said quantity of sulfur has been completely retained by the catalyser 11; the total quantity of sulfur present in the fuel is easily obtained by multiplying the total mass of fuel injected by the current value $S_{old}$ for sulfur concentration in the fuel.

$$S_{new} = S_{old} \cdot \frac{t_1 - t_0}{t_2 - t_0} \quad [2]$$

During the regeneration process to remove sulfur, the multisensor 14 detects lean operation ($\lambda$ less than 1) for as long as sulfur is present in the catalyser 11, whereas it detects rich operation ($\lambda$ greater than 1) when all the sulfur has been removed from the catalyser 11; in other words the time interval ($t_1-t_0$) is a function of the assumed quantity of sulfur retained in the catalyser 11 and estimated by means of the current sulfur concentration value $S_{old}$, while the time interval ($t_2-t_0$) is a function of the actual quantity of sulfur retained in the catalyser 11.

From the above explanation, it is clear that the regeneration process to remove sulfur is not complete until the multisensor 14 detects a change from lean ($\lambda$ less than 1) to rich ($\lambda$ greater than 1).

According to another embodiment, the size of the above-stated correction of the current sulfur concentration value Sold can be estimated by assuming that the dynamic sulfur filling process is faster than phenomena of drift in the engine 1 or of degradation of the catalyser 11, i.e. by assuming that any difference D between an estimated value $NO_{xstored1}$ of the total quantity of stored $NO_x$ groups by means of a model of $NO_x$ group production by the engine 1 and an estimated value $NO_{xstored2}$ of the total quantity of stored $NO_x$ groups on the basis of a storage model for the catalyser 11 is entirely attributable to an error in the current sulfur concentration value Sold (current value $S_{old}$ used in the storage model for the catalyser 11).

In particular, if the difference D is less than a predetermined threshold, said difference is attributed to an error in the current sulfur concentration value $S_{old}$ and is used to correct the current value $S_{old}$, while if the difference D is greater than the predetermined threshold, this indicates drift in the model of $NO_x$ group production by the engine 1 and is used to adjust the model itself.

The estimated value $NO_{xstored1}$ of the total quantity of stored $NO_x$ groups is determined by using a model of $NO_x$ group production by the engine 1; in particular, use of such a model provides subtraction from the quantity $NO_{xtotal}$ of $NO_x$ groups produced by the engine 1 of the quantity $NO_{xloss}$ of $NO_x$ groups not captured by the catalyser 11 and released directly into the atmosphere. As stated above, the quantity $NO_{xloss}$ of $NO_x$ groups not captured by the catalyser is obtained directly by the control unit 15 by measurement, performed by the multisensor 14, of the exhaust gases released from the exhaust pipe 9 into the atmosphere, while the quantity $NO_{xtotal}$ of $NO_x$ groups produced by the engine 1 is obtained in a substantially known manner by the control unit 15 using maps that state the specific quantity (i.e. the quantity per unit of fuel injected into the cylinders 2) of $NO_x$ groups produced by the engine 1 as a function of engine status (typically as a function of engine speed and as function of delivered torque).

The estimated value $NO_{xstored2}$ of the total quantity of stored $NO_x$ groups is determined by using a model of storage by the catalyser 11; said model is defined by a series of maps that state the quantity of $NO_x$ groups stored by the catalyser 11 as a function of the quantity $NO_{xtotal}$ of $NO_x$ groups produced by the engine 1 (obtained by applying the above-described model of $NO_x$ group production by the engine 1), as a function of the current sulfur concentration value Sold and as a function of the temperature of the gases present inside the catalyser (temperature provided by the multisensor 14).

Obviously, the above-mentioned models, and in particular the values stored in the respective maps, are determined in the laboratory by means of a series of tests carried out on the engine 1 equipped with a series of auxiliary measurement sensors, which are capable of providing an individual and accurate measurement of all the parameters involved in the operation of the engine 1 itself.

Preferably, the estimator 16 implements all three of the methods described above to estimate and/or correct the value S for sulfur concentration in the fuel, so that it is possible to compare the results obtained with at least two different methods and to identify any anomalous values due to malfunctioning or particular situations.

From the above explanation, it is clear that the estimator 16 is capable of determining the current value S for sulfur concentration in the fuel with a relatively high degree of precision; moreover, incorporating the estimator 16 inside the central control unit 15 is relatively economical and simple in that it does not involve the introduction of additional sensors, but simply modification at software level.

The invention claimed is:

1. Method for estimating sulfur content in fuel of an internal combustion engine (1) equipped with at least one cylinder (2) and at least one catalyser (11), said catalyser (11) being capable of storing a quantity of sulfur and $NO_x$ groups and being subjected to a regeneration process to remove $NO_x$ groups when efficiency (I) of the catalyser (11) falls outside an acceptable range, the method providing a determination of a percentage (S) of sulfur present in fuel supplied during a specific measurement time interval by dividing a quantity ($SO_{xstored}$) of sulfur stored in the catalyser (11) during the measurement time interval by a product of a fixed conversion constant ($K_{SOx}$) and a mass of fuel ($m_{fuel}$) supplied to the cylinder (2) in the measurement time interval, comprising the steps of estimating a first quantity ($NO_{xstored}$) of $NO_x$ groups stored by the catalyser (11) immediately before a regeneration process to remove $NO_x$ groups at a beginning of the measurement time interval, estimating a second quantity ($NO_{xstored}$) of $NO_x$ groups stored by the catalyser (11) immediately before a regeneration process to remove $NO_x$ groups at an end of the measurement time interval, and estimating said quantity ($SO_{xstored}$) of sulfur stored in the catalyser (11) during the measurement time interval from a difference between said first quantity ($NO_{xstored}$) of $NO_x$ groups and said second quantity ($NO_{xstored}$) of $NO_x$ groups, and obtaining each said quantity ($NO_{xstored}$) of $NO_x$ groups stored by the catalyser (11) by subtracting from a quantity ($NO_{xtotal}$) of $NO_x$ groups produced by the engine (1) a quantity ($NO_{xloss}$) of $NO_x$ groups not captured by the catalyser (11).

2. Method according to claim 1, wherein said quantity ($NO_{xloss}$) of $NO_x$ groups not captured by the catalyser (11) is measured by a sensor located downstream from the catalyser (11).

3. Method according to claim 1, wherein said quantity ($NO_{xtotal}$) of $NO_x$ groups produced by the engine (1) is estimated by using a model of $NO_x$ group production.

4. Method according to claim 3, wherein said model of $NO_x$ group production is defined by at least one map that states a specific quantity of $NO_x$ groups produced by the engine (1) as a function of engine status.

5. Method according to claim 1, wherein said efficiency (I) of the catalyser (11) is evaluated by an index (I) of deterioration in the performance of the catalyser (11), which index (I) is calculated by means of a ratio between a quantity ($NO_{xloss}$) of $NO_x$ groups not captured by the catalyser (11) and a quantity ($NO_{xtotal}$) of $NO_x$ groups produced by the engine (1).

6. Method for estimating a quantity ($SO_{xstored}$) of sulfur stored in a catalyser (11) of an internal combustion engine (1) equipped with at least one cylinder (2), said catalyser being capable of storing a quantity of sulfur and $NO_x$ groups and being subjected to a regeneration process to remove $NO_x$ groups when efficiency (I) of the catalyser (11) falls outside an acceptable range, comprising the steps of estimating a first quantity ($NO_{xstored}$) of $NO_x$ groups stored by the catalyser (11) immediately before a regeneration process to remove $NO_x$ groups at a beginning of a measurement time interval, estimating a second quantity ($NO_{xstored}$) of $NO_x$ groups stored by the catalyser (11) immediately before a regeneration process to remove $NO_x$ groups at an end of the measurement time interval, and estimating said quantity ($SO_{xstored}$) of sulfur stored in the catalyser (11) during the measurement time interval from a difference between said first quantity ($NO_{xstored}$) of $NO_x$ groups and said second quantity ($NO_{xstored}$) of $NO_x$ groups, and obtaining each said quantity ($NO_{xstored}$) of $NO_x$ groups stored by the catalyser (11) by subtracting from a quantity ($NO_{xtotal}$) of $NO_x$ groups produced by the engine (1) a quantity ($NO_{xloss}$) of $NO_x$ groups not captured by the catalyser (11).

7. Method according to claim 6, wherein said quantity ($NO_{xloss}$) of $NO_x$ groups not captured by the catalyser (11) is measured by a sensor (14) arranged downstream from the catalyser (11).

8. Method according to claim 6, wherein said quantity ($NO_{xtotal}$) of $NO_x$ groups produced by the engine (1) is estimated by using a model of $NO_x$ group production.

9. Method according to claim 8, wherein said model of $NO_x$ group production is defined by at least one map that states a specific quantity of $NO_x$ groups produced by the engine (1) as a function of engine status.

10. Method according to claim 6, wherein said efficiency (I) of the catalyser (11) is evaluated by an index (I) of deterioration in performance of the catalyser (11), and wherein said index (I) is calculated by means of a ratio between a quantity ($NO_{xloss}$) of $NO_x$ groups not captured by the catalyser (11) and a quantity ($NO_{xtotal}$) of $NO_x$ groups produced by the engine (1).

11. Method for estimating sulfur content in fuel of an internal combustion engine (1) equipped with at least one cylinder (2) and at least one catalyser (11), said catalyser (11) being capable of storing a quantity of sulfur and $NO_x$ groups and being subjected to a regeneration process to remove $NO_x$ groups when efficiency (I) of the catalyser (11) falls outside an acceptable range, the method providing a determination of a percentage (S) of sulfur present in fuel supplied during a specific measurement time interval by dividing a quantity ($SO_{xstored}$) of sulfur stored in the catalyser (11) during the measurement time interval by a product of a fixed conversion constant ($KSO_x$) and a mass of fuel ($m_{fuel}$) supplied to the cylinder (2) in the measurement time interval, comprising the steps of estimating a first quantity ($NO_{xstored}$) of $NO_x$ groups stored by the catalyser (11) immediately before a regeneration process to remove $NO_x$ groups at a beginning of the measurement time interval, estimating a second quantity ($NO_{xstored}$) of $NO_x$ groups stored by the catalyser (11) immediately before a regeneration process to remove $NO_x$ groups at an end of the measurement time interval, estimating said quantity ($SO_{xstored}$) of sulfur stored in the catalyser (11) during the measurement time interval from a difference between said first quantity ($NO_{xstored}$) of $NO_x$ groups and said second quantity ($NO_{xstored}$) of $NO_x$ groups, evaluating said efficiency (I) of the catalyser (11) by an index (I) of deterioration in the performance of the catalyser (11), and calculating said index (I) by means of the ratio between a quantity ($NO_{xloss}$) of $NO_x$ groups not captured by the catalyser (11) and a quantity ($NO_{xtotal}$) of $NO_x$ groups produced by the engine (1).

12. Method for estimating a quantity ($SO_{xstored}$) of sulfur stored in a catalyser (11) of an internal combustion engine (1) equipped with at least one cylinder (2), said the catalyser (11) being capable of storing a quantity of sulfur and $NO_x$ groups and being subjected to a regeneration process to remove $NO_x$ groups when efficiency (I) of the catalyser (11) falls outside an acceptable range, comprising the steps of estimating a first quantity ($NO_{xstored}$) of $NO_x$ groups stored by the catalyser (11) immediately before a regeneration process to remove $NO_x$ groups at a beginning of the measurement time interval, estimating a second quantity ($NO_{xstored}$) of $NO_x$ groups stored by the catalyser (11) immediately before a regeneration process to remove $NO_x$ groups at an end of the measurement time interval, estimating said quantity ($SO_{xstored}$) of sulfur stored in the catalyser (11) during the measurement time interval from a difference between said first quantity ($NO_{xstored}$) of $NO_x$ groups and said second quantity ($NO_{xstored}$) of $NO_x$ groups, evaluating said efficiency (I) of the catalyser (11) by an index (I) of deterioration in the performance of the catalyser (11), and calculating said index (I) by means of the ratio between a quantity ($NO_{xloss}$) of $NO_x$ groups not captured by the catalyser (11) and a quantity ($NO_{xtotal}$) of $NO_x$ groups produced by the engine (1).

* * * * *